United States Patent [19]

Cohen

[11] Patent Number: 5,633,254
[45] Date of Patent: May 27, 1997

[54] SYNERGISTIC FUNGICIDAL MIXTURES FOR THE CONTROL OF PLANT DISEASES

[75] Inventor: Yigal Cohen, Kiryat Ono, Israel

[73] Assignees: Agrogene Ltd.; C.T.S. Ltd., both of Israel

[21] Appl. No.: 583,909

[22] Filed: Jan. 11, 1996

[51] Int. Cl.⁶ .............. A01N 37/34; A01N 43/38; A01N 47/10; A61K 31/535
[52] U.S. Cl. .............. 514/237.5; 514/417; 514/476; 514/491; 514/525; 514/528
[58] Field of Search .............. 514/528, 237.5, 514/491, 417, 525, 476

[56] References Cited

U.S. PATENT DOCUMENTS

| | | | |
|---|---|---|---|
| 3,957,847 | 5/1976 | Davidson | 260/465.4 |
| 4,101,669 | 7/1978 | Baude et al. | 424/286 |
| 4,742,079 | 5/1988 | Devoiser Lambert et al. | 514/528 |
| 4,923,866 | 5/1990 | Albert et al. | 514/237.5 |
| 4,927,823 | 5/1990 | Gisi | 514/237.5 |
| 5,262,414 | 11/1993 | Albert et al. | 514/237.5 |

FOREIGN PATENT DOCUMENTS 0 120 321 B1  5/1988  European Pat. Off. .

*Primary Examiner*—Allen J. Robinson
*Attorney, Agent, or Firm*—Mark M. Friedman

[57] ABSTRACT

Synergistic mixtures which include dimethomorph and cymoxonil in a fungicidially effective aggregate amount, and the use of such mixtures in the control of plant diseases. In certain embodiments, a contact fungicide is included, along with the dimethomorph and cymoxonil in suitable ratios.

13 Claims, No Drawings

5,633,254

SYNERGISTIC FUNGICIDAL MIXTURES FOR THE CONTROL OF PLANT DISEASES

FIELD AND BACKGROUND OF THE INVENTION

The present invention relates to fungicides, more particularly to oomycetes controlling fungicides.

Although a wide variety of oomycetes controlling fungicides are known, the need exists for still more effective fungicides.

SUMMARY OF THE INVENTION

It has been found that the use of cymoxanil, trademark "Curzate" (U.S. Pat. No. 3,957,847), in association with dimethomorph is particularly effective in combatting or preventing fungal diseases.

DESCRIPTION OF THE PREFERRED EMBODIMENTS

The invention accordingly provides a method to combat fungal diseases in plants which comprises applying to the plants, seeds or soil, in admixture, a fungicidally effective aggregate amount of cymoxanil and dimethomorph.

Cymoxanil is a known fungicide. It has a local systemic fungicidal activity against, i.a., Plasmopara spp and Phytophthora spp.

Dimethomorph, which is disclosed in European Patent Application 120321, shows fungicidal activity with relatively low systemic activity against oomycetes such as Plasmopara spp and Phytophtora spp.

The use of dimethomorph in combination with cymoxanil surprisingly and substantially enhances the fungicidal effectiveness of cymoxanil, and vice versa. The method of the invention may particularly be useful to delay the development of dimethomorph-resistant oomycetes strains, especially field strains of Plasmopara spp and of Phytophtora spp. The method of the invention decreases the risk of fungal subpopulation developing resistance against dimethomorph. It is surprisingly effective against oomycetes strains which are sensitive or which have already developed resistance against phenylamide fungicides such as metalaxyl and oxadixyl.

The method of the invention is particularly suitable for use against fungi of the class oomycetes such as Phytophthora spp, Plasmopara spp, Peronospora spp, Pseudoperonospora spp, Sclerophthora spp and Bermia spp in crops such as grapevines, tomato, hops, cacao, tobacco, potato, peas, onions, cucurbits, crucifers or lettuce cultures or turf.

Examples of fungus/crop systems against which the method of the invention is particularly indicated are *Pseudoperonospora cubensis* in cucurbits, *Plasmopara viticola* in grapevines and most particularly *Phytophthora infestans* in potatoes and tomatoes.

The cymoxanil and dimethomorph may for example be applied in spray form, e.g., employing appropriate dilutions of a soluble concentrate or of a wettable powder formulation in water.

Suitable fungicidally effective aggregate amounts of cymoxanil and dimethomorph lie in the range of from about 550 to about 1000 g/ha of crop locus. In general, satisfactory results will be obtained when employing from about 300 to about 500 g/ha, e.g., about 400 g/ha of cymoxanil and from about 150 to about 400 g/ha, e.g., 250 g/ha, of dimethomorph.

The application rate may also be expressed in terms of concentrations. Spray liquors suitable for use in, for example, grapevines or potatoes comprise from about 50 to about 100 g per hectoliter. The spray treatment involves usually foliar application till the run-off. This corresponds, in general, with a spray volume of from about 600 to about 1000 liters per hectare of crop locus, depending on the growth stage of the crop.

Other pesticides, e.g., fungicides, bactericide, insecticides, acaricides, herbicides or plant growth regulating agents, may be used in addition to cymoxanil and dimethomorph to enhance the activity of the association of the invention or to widen its spectrum of activity. The addition of a contact fungicide is particularly advantageous.

The term contact fungicide as used herein is intended to relate to fungicides having no, or no significant, systemic action and comprises, by way of example, copper fungicides; ethylene bis[dithiocarbamato]metal compounds such as mancozeb, maneb, zineb and propineb; captan; captafol; folpet; and chlorothalonil.

The weight ratio cymoxanil:dimethomorph will depend on various factors such as the mode of application, the disease to be combatted, the crop involved, the application time, etc.

In general, satisfactory results will be obtained when the weight ratio of cymoxanil:dimethomorph lies in the range of from about 1:3 to about 3:1, more preferably from about 2:1 to about 1:2, as illustrated by the experimental test results for the range of from about 1.5:1 to about 1:1.5.

The invention also provides fungicidal compositions comprising cymoxanil and dimethomorph, e.g., in a weight ratio within the range specified hereinabove.

The method of the invention is particularly useful when a contact fungicide is admixed with cymoxanil and dimethomorph.

In general, satisfactory results will be obtained when the weight ratio of contact fungicide:cymoxanil:dimethomorph lies in the range of from about 10:5:1 to 5:1:1, more preferably from about 7.5:1.5:1 to 10:1:1 and most preferably at a ratio of about 5.15:1.5:1, as illustrated by the experimental test results.

The invention also provides fungicidal compositions comprising a contact fungicide (e.g., mancozeb, folpet, chlorothalonil), cymoxanil and dimethomorph.

Such compositions of the invention may be formulated in any conventional form, for example in the form of a twin packet, triple packet or of an emulsifiable concentrate, a soluble concentrate, a wettable powder or water dispersible granule. Such compositions may be produced in conventional manner, for example by mixing cymoxanil with dimethomorph with appropriate adjuvants such as diluents and optionally other formulating ingredients such as surfactants.

The term diluent as used herein means any liquid or solid agriculturally acceptable material, including carriers, which may be added to the active constituents to bring them in a suitable application or commercial form. It can, for example, be talc, kaolin, diatomaceous earth, mineral oil or water.

Particular formulations to be applied in spraying forms such as water, dispersible concentrates or wettable powders, may contain surfactants such as wetting and dispersing agents, e.g., the condensation product of formaldehyde with naphthalene sulphonate, an alkylarysulphonate, a lignin sulphonate, a fatty sulphate, an ethoxylated alkylphenol and an ethoxylated fatty alcohol.

In general, the formulations include from 0.01 to 90% by weight of active agent, from 0 to 20% of an agriculturally acceptable surfactant and 10 to 99.99% solid or liquid diluent, the active agent consisting of cymoxanil and dimethomorph, with or without a contact fungicide such as mancozeb. The formulations may additionally contain additives such as pigments, thickeners and the like.

The invention is illustrated by the following examples, wherein parts and percentages are by weight.

TEST METHODS

Determination Of Fungicidal Activity (EC 90) Phytophtora infestans On Potato Potted potato plants (9–12 leaf stage) are sprayed with an aqueous spray liquid comprising 250, 63, 16 and 4 ppm of cymoxanil, dimethomorph, a contact fungicide, a mixture of cymoxanil with dimethomorph in various weight ratios or a mixture of cymoxanil, dimethomorph and a contact fungicide in various weight ratios. The compounds cymoxanil and dimethomorph are employed in aqueous solution of the wettable powder formulation. The mixtures of cymoxanil and dimethomorph, or of both of them together with a contact fungicide, are employed as tank mixtures thereof.

One day after the fungicide treatment, the treated plant leaves are inoculated with a sporangium suspension ($3 \times 10^3$ sporangia/ml) of *Phytophthora infestans*. Sporangia are taken from inoculated potato tuber slices. The plants are then transferred to a dew chamber providing 100% relative atmospheric humidity at an ambient temperature of 18° C. in the dark. Disease control is evaluated 5–8 days thereafter, by comparing the treated plants (leaves) with untreated, similarly inoculated plants (leaves).

The inoculation is performed by using either sensitive fungal strains or strains which developed resistance against phenylamide fungicides.

The disease control is expressed for each test concentration as % control. This allows the determination of the EC 90 exp. value using probit analysis, i.e., the concentration of each compound or combination allowing 90% disease control.

The experimental results (EC 90 exp.) for a given weight ratio cymoxanil:dimethomorph is compared with the corresponding EC 90 theor. value, i.e., the concentration of that particular mixture allowing 90% disease control calculated according to Wadley.

$$EC(I+II)90 \text{ theor.} = \frac{(a+b)}{\frac{a}{EC(I)90 \text{ exp.}} + \frac{b}{EC(II)90 \text{ exp.}}}$$

wherein a and b are the ratios of cymoxanil and dimethomorph in the mixture, respectively, and the indexes (I), (II) and (I+II) refer to cymoxanil, dimethomorph and the a+b mixture of cymoxanil and dimethomorph. In the case of synergism, EC(I+II)90 theor. is greater than EC(I+II)90 exp., or $$SF=[EC(I+II)90 \text{ theor.}]/[EC(I+II)90 \text{ exp.}] > 1$$

The experimental results (EC 90 exp.) for a given weight ratio of a contact fungicide:cymoxanil:dimethomorph is compared with the corresponding EC 90 theor. value, i.e., the concentration of that particular triple mixture allowing 90% disease control calculated according to Wadley.

$$EC(I+II+\text{contact})90 \text{ theor.} = \frac{a+b+c}{\frac{a}{EC(I)90 \text{ exp.}} + \frac{b}{EC(II)90 \text{ exp.}} + \frac{c}{EC(\text{contact})90 \text{ exp.}}}$$

wherein a, b and c are the ratios of cymoxanil, dimethomorph and the contact fungicide in the mixture, respectively, and the indexes I, II, and III refer to cymoxanil, dimethomorph, the contact fungicide and the a+b+c mixture of the three components, respectively. In the case of synergism, EC(I+II+III)90 theor. is greater than EC(I+II+III)90 exp., or $$SF=[EC(I+II+III)90 \text{ theor.}]/[EC(I+II+III)90 \text{ exp.}] > 1$$

TEST METHODS

Determination Of Fungicidal Activity (EC 90) Pseuduperonospora cubensis On Cucumber Young potted cucumber plants (2 leaf stage) were sprayed with fungicides as described above for potatoes. Inoculation was done one day after the treatment with sporangium suspension ($1.5 \times 10^3$ /ml) of *Pseudoperonospora cubensis*. Inoculation, disease assessment and calculation of EC 90 were conducted as described for *P. infestans* in potato.

TEST RESULTS

The fungicidal activity obtained with cymoxanil (in aqueous spray liquid form of a 50% wettable powder formulation; dimethomorph (in aqueous spray liquid form of a 25% wettable powder formulation; cymoxanil + dimethomorph mixtures in weight ratio 2:1, 1.5:1, 1:1, 1:1.5 and 1:2, against a *Phytophthora infestans* is expressed in Table I. The EC 90 exp. values for cymoxanil and dimethomorph specified in Table I have been employed to calculate the EC 90 theor. values for the cymoxanil/dimethomorph mixtures expressed in Table I.

TABLE I

| | *P. infestans* in potato | | | | | | |
|---|---|---|---|---|---|---|---|
| Concentration | % Control | | | | EC 90 exp. | EC 90 theor. | |
| ppm (a.i.) | 250 | 63 | 16 | 4 | (ppm) | (ppm) | SF |
| Cymoxanil | 97 | 93 | 84 | 51 | 104 | — | — |
| Dimethomorph | 100 | 97 | 87 | 63 | 30 | — | — |
| Cymoxanil to Dimethomorph Weight Ratio | | | | | | | |
| 1:1 | 97 | 97 | 84 | 53 | 96 | 48 | 0.5 |
| 1.5:1 | 100 | 100 | 87 | 71 | 15 | 53 | 3.5 |
| 2:1 | 97 | 95 | 60 | 53 | 108 | 54 | 0.5 |
| 1:1.5 | 97 | 97 | 73 | 53 | 100 | 40 | 0.4 |
| 1:2 | 68 | 57 | 51 | 51 | 435 | 44 | 0.1 |

The fungicidal activity obtained with cymoxanil (as above), dimethomorph (as above), the contact fungicide mancozeb (in aqueous spray liquid of 80% wettable powder), cymoxanil + dimethomorph + mancozeb in weight ratios of 10.5:1:1, 7.5:1.5:1, 5.15:1.5:1 against *Phytophthora infestans* is expressed in Table II. The EC 90 exp. values for cymoxanil, dimethomorph and mancozeb specified in Table II have been employed to calculate the EC 90 theor. values for the mixtures expressed in Table II.

TABLE II

*P. infestans* in potato

| Concentration | % Control | | | | EC 90 exp. | EC 90 theor. | |
|---|---|---|---|---|---|---|---|
| ppm (a.i.) | 250 | 63 | 16 | 4 | (ppm) | (ppm) | SF |
| Mancozeb | 45 | 27 | 20 | 13 | 550 | — | — |
| Cymoxanil | 97 | 93 | 84 | 51 | 104 | — | — |
| Dimethomorph | 100 | 97 | 87 | 63 | 30 | — | — |
| Mancozeb to Cymoxanil to Dimethomorph Weight Ratios: | | | | | | | |
| 10.5:1:1 | 89 | 83 | 63 | 60 | 209 | 209 | 1.0 |
| 7.5:1.5:1 | 100 | 76 | 73 | 57 | 78 | 164 | 2.1 |
| 5.15:1.5:1 | 100 | 100 | 73 | 68 | 20 | 134 | 6.7 |

The fungicidal activity obtained for the triple mixture mancozeb + cymoxanil + dimethomorph in controlling *Pseudoperonospora cubensis* in cucumbers is illustrated in Table III.

TABLE III

*Pseudoperonospora cubensis* on cucumber

| Concentration | % Control | | | | EC 90 exp. | EC 90 theor. | |
|---|---|---|---|---|---|---|---|
| ppm (a.i.) | 250 | 63 | 16 | 4 | (ppm) | (ppm) | SF |
| Mancozeb | 100 | 90 | 61 | 8 | 54 | — | — |
| Cymoxanil | 82 | 61 | 23 | 5 | 258 | — | — |
| Dimethomorph | 100 | 100 | 78 | 67 | 18 | — | — |
| Mancozeb to Cymoxanil to Dimethomorph Weight Ratios: | | | | | | | |
| 5.15:1.5:1 | 100 | 100 | 100 | 74 | 16 | 53 | 3.1 |

The fungicidal activity of the invented triple mixture of mancozeb + cymoxanil + dimethomorph at a near optimal ratio (5.15:1.5:1) was higher than that of either the commercial dual mixture "Mancur" (mancozeb + cymoxanil) or the commercial dual mixture "Acrobat" (mancozeb + dimethomorph). This higher activity is illustrated in Table IV for the control of *Phytophthora infestans* in potato.

TABLE IV

*Phytophtora infestans* in potato

| Concentration | % Control | | | | EC 90 exp. |
|---|---|---|---|---|---|
| ppm (a.i.) | 250 | 63 | 16 | 4 | (ppm) |
| Mancozeb + Cymoxanil 4:1 | 100 | 95 | 85 | 40 | 37 |
| Mancozeb + Dimethomorph 6.7:1 | 100 | 90 | 44 | 40 | 58 |
| Mancozeb to Cymoxanil to Dimethomorph Weight Ratios: | | | | | |
| 5.15:1.5:1 | 100 | 100 | 90 | 86 | 13 |
| 11:1:1 | 98 | 95 | 85 | 63 | 82 |
| 16:2.4:1 | 100 | 95 | 75 | 75 | 40 |

As can be seen, the best EC 90 was obtained with a ratio of 5.15:1.5:1.

The test results presented in Table V demonstrate a synergistic effect for the triple mixture between mancozeb + cymoxanil + dimethomorph in controlling *P. Infestans* in potted potato plants incubated for 5 days outdoors after fungicidal spray.

TABLE V

*Phytophtora infestans* in potato

| Concentration | % Control | | | | EC 90 exp. | EC 90 theor. | |
|---|---|---|---|---|---|---|---|
| ppm (a.i.) | 250 | 63 | 16 | 4 | (ppm) | (ppm) | SF |
| Mancozeb | 74 | 65 | 58 | 31 | 336 | — | — |
| Cymoxanil | 65 | 39 | 10 | 0 | 343 | — | — |
| Dimethomorph | 96 | 80 | 66 | 28 | 144 | — | — |
| Mancozeb to Cymoxanil to Dimethomorph Weight Ratio: | | | | | | | |
| 5.15:1.5:1 | 100 | 82 | 77 | 56 | 65 | 286 | 4.4 |

The test results presented in Table VI demonstrate the efficacy of triple mixtures composed of mancozeb + cymoxanil + dimethomorph applied once in 2 weeks in controlling *P. infestans* under field conditions.

TABLE VI

*Phytophtora infestans* in potato

| Fungicide mixture a.i./ha in g and weight ratio | Number of leaflets infected per plot at various times after inoculation | | |
|---|---|---|---|
| | at 2 weeks | at 3 weeks | at 3.5 weeks |
| None | 58 ± 20* | 2050 ± 230* | 2225 ± 228* |
| Metalaxyl + mancozeb 1905 g 1:7.5 | 0 | 21 ± 11* | 43 ± 19* |
| Ofurace + folpet 2050 g 1:7.5 | 0 | 103 ± 20* | 220 ± 84* |
| Dimethomorph + cymoxanil + mancozeb 2190 g 1:1.5:5.15 | 0 | 2 ± 1** | 4 ± 2** |
| 2238 g 1:1.5:7.5 | 0 | 3 ± 1** | 8 ± 4** |

Note: The first spray was given 1 day before inoculation while the second spray was given 14 days after inoculation.
*sporulating lesions
**non-sporulating lesions

FORMULATION EXAMPLE 1

| | |
|---|---|
| 15% | cymoxanil |
| 10.% | dimethomorph |
| 5% | silicagel |
| 62% | kaolin |
| 5% | sodium ligninsulphonate |
| 3% | sodium dodecylsulphate |

FORMULATION EXAMPLE 2

| | |
|---|---|
| 16.8% | mancozeb |
| 4.9% | cymoxanil |
| 3.3% | dimethomorph |
| 5% | silicagel |
| 62% | kaolin |
| 5% | sodium ligninsulphonate |
| 3% | sodium dodecylsulphae |

FORMULATION EXAMPLE 3

| | |
|---|---|
| 18.75% | mancozeb |
| 3.75% | cymoxanil |
| 2.5% | dimethomorph |
| 5% | silicagel |
| 62% | kaolin |
| 5% | sodium ligninsulphonate |
| 3% | sodium dodecylsulphae |

The wettable powders of Formulation Examples 1 to 3 are obtained by mixing of the components, subsequent milling of the mixture in an appropriate mill allowing a sufficiently fine particle size (equal to or smaller than 20 micrometer) followed by mixing of the milled material.

While the invention has been described with respect to a limited number of embodiments, it will be appreciated that many variations, modifications and other applications of the invention may be made.

What is claimed is:

1. A method of combatting phytophogenic fungi which comprises applying to the plants cymoxanil and dimethomorph in a synergistic fungicidally effective aggregate amount wherein the weight ratio of cymoxanil to dimethomorph is about 1.5:1, and the aggregate amount of cymoxanil and dimethomorph lies in the range of from about 550 to about 1000 g per hectare of crop locus.

2. The method of claim 1 wherein the phytopathogenic fungi are of the class oomycetes.

3. The method of claim 2, wherein the fungi are Phytophthora spp, Pseudoperonospora spp, Peronospora spp, Plasmopara spp or Bremia spp.

4. The method of claim 3, wherein the plants are tomato, potato, grapevine, tobacco, crucifers or cucurbit cultures.

5. A method of combating phytopathogenic fungi which comprises applying to the plant:

(a) cymoxanil;

(b) dimethomorph; and (c) a contact fungicide selected from the group consisting of folpet, chlorothalonil and mancozeb, in a synergistically fungicidally aggregate amount, wherein the weight ratio of contact fungicide to cymoxanil to dimethomorph is in a range from about 7.5:1.5:1 to about 5:1.5:1.

6. The method of claim 5, wherein the weight ratio of contact fungicide to cymoxanil to dimethomorph is about 5.15:1.5:1.

7. The method of claim 5, wherein the phytopathogenic fungi are of the class oomycetes.

8. The method of claim 5, wherein the fungi are Phytophthora spp, Pseudoperonospora spp, Peronospora spp, Plasmopara spp or Bremia spp.

9. The method of claim 5, wherein the plants are tomato, potato, grapevine, tobacco or cucurbit cultures.

10. The method of claim 5, wherein the aggregate amount of cymoxanil, dimethomorph and the contact fungicide lies in the range of from about 1000 to about 4000 g per hectare of crop locus.

11. The method of claim 7, wherein the aggregate amount of cymoxanil, dimethomorph and the contact fungicide lies in the range of from about 1000 to about 4000 g per hectare of crop locus.

12. The method of claim 8, wherein the aggregate amount of cymoxanil, dimethomorph and the contact fungicide lies in the range of from about 1000 to about 4000 g per hectare of crop locus.

13. The method of claim 9, wherein the aggregate amount of cymoxanil, dimethomorph and the contact fungicide lies in the range of from about 1000 to about 4000 g per hectare of crop locus.

* * * * *